(12) United States Patent
Meier et al.

(10) Patent No.: US 9,814,584 B2
(45) Date of Patent: Nov. 14, 2017

(54) FIXED-BEARING KNEE PROSTHESIS HAVING A LOCKING MECHANISM WITH A CONCAVE-TO-CONVEX MATING INTERFACE

(75) Inventors: Rusty T. Meier, Warsaw, IN (US); Daren L. Deffenbaugh, Winona Lake, IN (US); Mark A. Heldreth, Mentone, IN (US); Stephen A. Hazebrouck, Winona Lake, IN (US)

(73) Assignee: DEPUY IRELAND UNLIMITED COMPANY (IE)

( * ) Notice: Subject to any disclaimer, the term of this patent is extended or adjusted under 35 U.S.C. 154(b) by 727 days.

(21) Appl. No.: 13/247,453

(22) Filed: Sep. 28, 2011

(65) Prior Publication Data
US 2013/0079885 A1   Mar. 28, 2013

(51) Int. Cl.
  *A61F 2/38*   (2006.01)
  *A61F 2/30*   (2006.01)
(52) U.S. Cl.
  CPC ............ *A61F 2/38* (2013.01); *A61F 2/389* (2013.01); *A61F 2002/305* (2013.01); *A61F 2002/30172* (2013.01); *A61F 2002/30181* (2013.01); *A61F 2002/30329* (2013.01); *A61F 2002/30604* (2013.01); *A61F 2002/30616* (2013.01); *A61F 2002/30878* (2013.01)
(58) Field of Classification Search
  CPC .................................. A61F 2/38; A61F 2/389
  USPC .............................. 623/20.21, 20.32, 20.34
  See application file for complete search history.

(56) References Cited

U.S. PATENT DOCUMENTS

| | | | |
|---|---|---|---|
| 4,257,129 A | 3/1981 | Volz | |
| 4,673,407 A | 6/1987 | Martin | |
| 4,714,474 A | 12/1987 | Brooks et al. | |
| 4,795,468 A | 1/1989 | Hodorek et al. | |
| 4,822,362 A | 4/1989 | Walker et al. | |
| 4,944,757 A | 7/1990 | Martinez et al. | |

(Continued)

FOREIGN PATENT DOCUMENTS

| | | | |
|---|---|---|---|
| EP | 0495340 A1 | 7/1992 | |
| EP | 2042134 A1 | 4/2009 | |

(Continued)

OTHER PUBLICATIONS

European Search Report for Application No./Patent No. 12186668. 5-2310, dated Nov. 8, 2012, 6 pages.

*Primary Examiner* — Bruce E Snow
*Assistant Examiner* — Melissa Hoban
(74) *Attorney, Agent, or Firm* — Barnes & Thornburg LLP

(57) ABSTRACT

A fixed-bearing prosthesis includes a femoral component having a medial condyle surface and a lateral condyle surface. The knee prosthesis also includes a bearing having a medial bearing surface configured to articulate with the medial condyle surface of the femoral component, and a lateral bearing surface configured to articulate with the lateral condyle surface of the femoral component. A tibial tray is secured to the bearing. The tibial tray has a platform with an elongated stem extending downwardly from a lower surface thereof. A posterior buttress extends along a posterior section of the perimeter of the tray's platform, and an anterior buttress extends along an anterior section of the perimeter of the tray's platform. Differently-sized tibial trays are interchangeable with differently-sized bearings.

15 Claims, 4 Drawing Sheets

(56) References Cited

U.S. PATENT DOCUMENTS

| | | |
|---|---|---|
| 5,271,737 A | 12/1993 | Baldwin et al. |
| 5,344,460 A | 9/1994 | Turanyi et al. |
| 5,370,699 A | 12/1994 | Hood et al. |
| 5,405,396 A | 4/1995 | Heldreth et al. |
| 5,413,604 A | 5/1995 | Hodge |
| 5,480,446 A | 1/1996 | Goodfellow et al. |
| 5,702,463 A | 12/1997 | Pothier et al. |
| 5,824,103 A | 10/1998 | Williams |
| 5,871,545 A | 2/1999 | Goodfellow et al. |
| 5,879,394 A | 3/1999 | Ashby et al. |
| 5,957,979 A | 9/1999 | Beckman et al. |
| 5,964,808 A | 10/1999 | Blaha et al. |
| 6,039,764 A | 3/2000 | Pottenger et al. |
| 6,068,658 A | 5/2000 | Insall et al. |
| 6,090,144 A | 7/2000 | Letot et al. |
| 6,162,254 A | 12/2000 | Timoteo |
| 6,299,646 B1 | 10/2001 | Chambat et al. |
| 6,379,388 B1 | 4/2002 | Ensign et al. |
| 6,869,448 B2 | 3/2005 | Tuke et al. |
| 7,771,484 B2 * | 8/2010 | Campbell .................. 623/20.34 |
| 2004/0215345 A1 | 10/2004 | Perrone, Jr. et al. |
| 2005/0021147 A1 | 1/2005 | Tarabichi |
| 2005/0209702 A1 | 9/2005 | Todd et al. |
| 2008/0243263 A1 * | 10/2008 | Lee et al. ................... 623/20.33 |
| 2009/0088859 A1 * | 4/2009 | Hazebrouck et al. ..... 623/20.14 |
| 2010/0063594 A1 * | 3/2010 | Hazebrouck et al. ..... 623/20.29 |
| 2013/0046385 A1 * | 2/2013 | Hartdegen et al. ........ 623/20.34 |

FOREIGN PATENT DOCUMENTS

| | | |
|---|---|---|
| FR | 2653992 B1 | 1/1998 |
| WO | 9966864 A1 | 12/1999 |

* cited by examiner

FIXED-BEARING KNEE PROSTHESIS HAVING A LOCKING MECHANISM WITH A CONCAVE-TO-CONVEX MATING INTERFACE

TECHNICAL FIELD

The present disclosure relates generally to an implantable orthopaedic prosthesis, and more particularly to an implantable knee prosthesis.

BACKGROUND

During the lifetime of a patient, it may be necessary to perform a joint replacement procedure on the patient as a result of, for example, disease or trauma. The joint replacement procedure may involve the use of a prosthesis which is implanted into one or more of the patient's bones. In the case of a knee replacement procedure, a tibial tray is implanted into the patient's tibia. A bearing is secured to the tibial tray. The condyle surfaces of a replacement femoral component bear against the tibial bearing.

One type of knee prosthesis is a fixed-bearing knee prosthesis. As its name suggests, the bearing of a fixed-bearing knee prosthesis does not move relative to the tibial tray. Fixed-bearing designs are commonly used when the condition of the patient's soft tissue (i.e., knee ligaments) does not allow for the use of a knee prosthesis having a mobile bearing.

The components of a fixed-bearing knee prosthesis are typically provided by the manufacturer in matching sizes. Specifically, most currently available fixed-bearing knee prostheses allow the surgeon to use a number of bearing sizes for a particular size of femoral component, but each bearing size is generally matched to a particular size of tibial tray.

SUMMARY

According to one aspect, a fixed-bearing knee prosthesis includes a femoral component having a medial condyle surface and a lateral condyle surface. The prosthesis also includes a bearing having a medial bearing surface configured to articulate with the medial condyle surface of the femoral component, and a lateral bearing surface configured to articulate with the lateral condyle surface of the femoral component. A tibial tray is secured to the bearing. The tibial tray has a platform with a fixation member extending inferiorly from an inferior surface of the platform. The platform includes a posterior buttress extending anteriorly away from a posterior section of a perimeter of the platform and extending superiorly from a superior surface of the platform. The posterior buttress includes a lateral-most edge having a convex surface that transitions to a concave surface, and a medial-most edge having a convex surface that transitions to a concave surface.

The posterior buttress of the tibial tray includes a superior-most surface, with the posterior buttress extending superiorly from the superior surface of the platform to the superior-most surface of the posterior buttress. The convex surface of the lateral-most edge of the posterior buttress extends inferiorly from the superior-most surface of the posterior buttress and transitions to the concave surface of the lateral-most edge of the posterior buttress. Similarly, the convex surface of the medial-most edge of the posterior buttress extends inferiorly from the superior-most surface of the posterior buttress and transitions to the concave surface of the medial-most edge of the posterior buttress.

The concave surface of the lateral-most edge of the posterior buttress extends inferiorly from the convex surface of the lateral-most edge of the posterior buttress and transitions to the superior surface of the platform. Similarly, the concave surface of the medial-most edge of the posterior buttress extends inferiorly from the convex surface of the medial-most edge of the posterior buttress and transitions to the superior surface of the platform.

The posterior buttress is generally Y-shaped and has a first arm extending along a posterior edge of the platform and a second arm extending along the posterior edge of the platform in a direction away from the first arm. The lateral-most edge of the posterior buttress is defined in the first arm, with the medial-most edge of the posterior buttress being defined in the second arm. A third arm extends anteriorly away from the first arm and the second arm.

The lateral-most edge of the posterior buttress is defined in the third arm such that the lateral-most edge of the posterior buttress extends anteriorly away from the posterior edge of the platform along the first arm of the posterior buttress and transitions to the third arm. On the opposite side, the medial-most edge of the posterior buttress is defined in the third arm such that the medial-most edge of the posterior buttress extends anteriorly away from the posterior edge of the platform along the second arm of the posterior buttress and transitions to the third arm.

The posterior buttress of the tibial tray includes an anterior-most edge. The lateral-most edge of the posterior buttress extends anteriorly away from the first arm along the third arm of the posterior buttress and transitions to the anterior-most edge of the posterior buttress. The medial-most edge of the posterior buttress extends anteriorly away from the second arm along the third arm of the posterior buttress and transitions to the anterior-most edge of the posterior buttress.

The bearing has a superior surface and an inferior surface. Both the medial bearing surface and the lateral bearing surface are defined in the superior surface of the bearing. The inferior surface of the bearing contacts the superior surface of the platform of the tibial tray. The inferior surface of the bearing has a posterior recess formed therein, with the posterior buttress of the tibial tray being positioned in the posterior recess of the bearing.

The posterior recess of the bearing is defined by a lateral-most sidewall that extends superiorly from an inferior-most surface of the bearing, and a medial-most sidewall that extends superiorly from the inferior-most surface of the bearing. The lateral-most sidewall includes a convex surface that transitions to a concave surface, with the medial-most sidewall likewise including a concave surface that transitions to a convex surface.

The convex surface of the lateral-most sidewall of the posterior recess extends superiorly from the inferior-most surface of the bearing and transitions to the concave surface of the lateral-most sidewall of the posterior recess. Similarly, the convex surface of the medial-most sidewall of the posterior recess extends superiorly from the inferior-most surface of the bearing and transitions to the concave surface of the medial-most sidewall of the posterior recess.

According to another aspect, a fixed-bearing knee prosthesis includes a femoral component having a medial condyle surface and a lateral condyle surface. The prosthesis also includes a bearing having a medial bearing surface configured to articulate with the medial condyle surface of the femoral component, and a lateral bearing surface configured to articulate with the lateral condyle surface of the femoral component. A tibial tray is secured to the bearing. The tibial tray has a platform with a fixation member extending inferiorly from an inferior surface of the platform. The platform has an anterior buttress extending along an anterior section of a perimeter of the platform and extending superiorly from a superior surface of the platform. The anterior buttress includes a posterior-most edge that includes a convex surface that transitions to a concave surface.

The anterior buttress of the tibial tray includes a superior-most surface. The anterior buttress extends superiorly from the superior surface of the platform to the superior-most surface of the posterior buttress. The convex surface of the posterior-most edge of the anterior buttress extends inferiorly from the superior-most surface of the anterior buttress and transitions to the concave surface of the posterior-most edge of the posterior buttress.

The concave surface of the posterior-most edge of the anterior buttress extends inferiorly from the convex surface of the posterior-most edge of the anterior buttress and transitions to the superior surface of the platform.

The bearing has a superior surface and an inferior surface, with both the medial bearing surface and the lateral bearing surface being defined in the superior surface of the bearing. The inferior surface of the bearing contacts the superior surface of the platform of the tibial tray. The inferior surface of the bearing has an anterior recess formed therein, with the anterior buttress of the tibial tray being positioned in the anterior recess of the bearing.

The anterior recess of the bearing is defined by a posterior-most sidewall that extends superiorly from an inferior-most surface of the bearing. The posterior-most sidewall includes a convex surface that transitions to a concave surface.

The convex surface of the posterior-most sidewall of the anterior recess extends superiorly from the inferior-most surface of the bearing and transitions to the concave surface of the posterior-most sidewall of the anterior recess.

An imaginary line extends along the posterior-most edge of the anterior buttress, with such an imaginary line defining a curve having a constant radius.

The posterior-most edge of the anterior buttress has an undercut defined therein, with such an undercut being centered on the midpoint of the imaginary line.

The bearing includes a locking tab positioned in the undercut defined in the anterior buttress.

The medial end of the anterior buttress is located at a location on the anterior edge of the platform between an anterior-most point of the platform and a medial-most point of the platform, with the lateral end of the anterior buttress being located at a location on the anterior edge of the platform between the anterior-most point of the platform and a lateral-most point of the platform.

BRIEF DESCRIPTION OF THE DRAWINGS

The detailed description particularly refers to the following figures, in which.

DETAILED DESCRIPTION OF THE DRAWINGS

Figure 1:
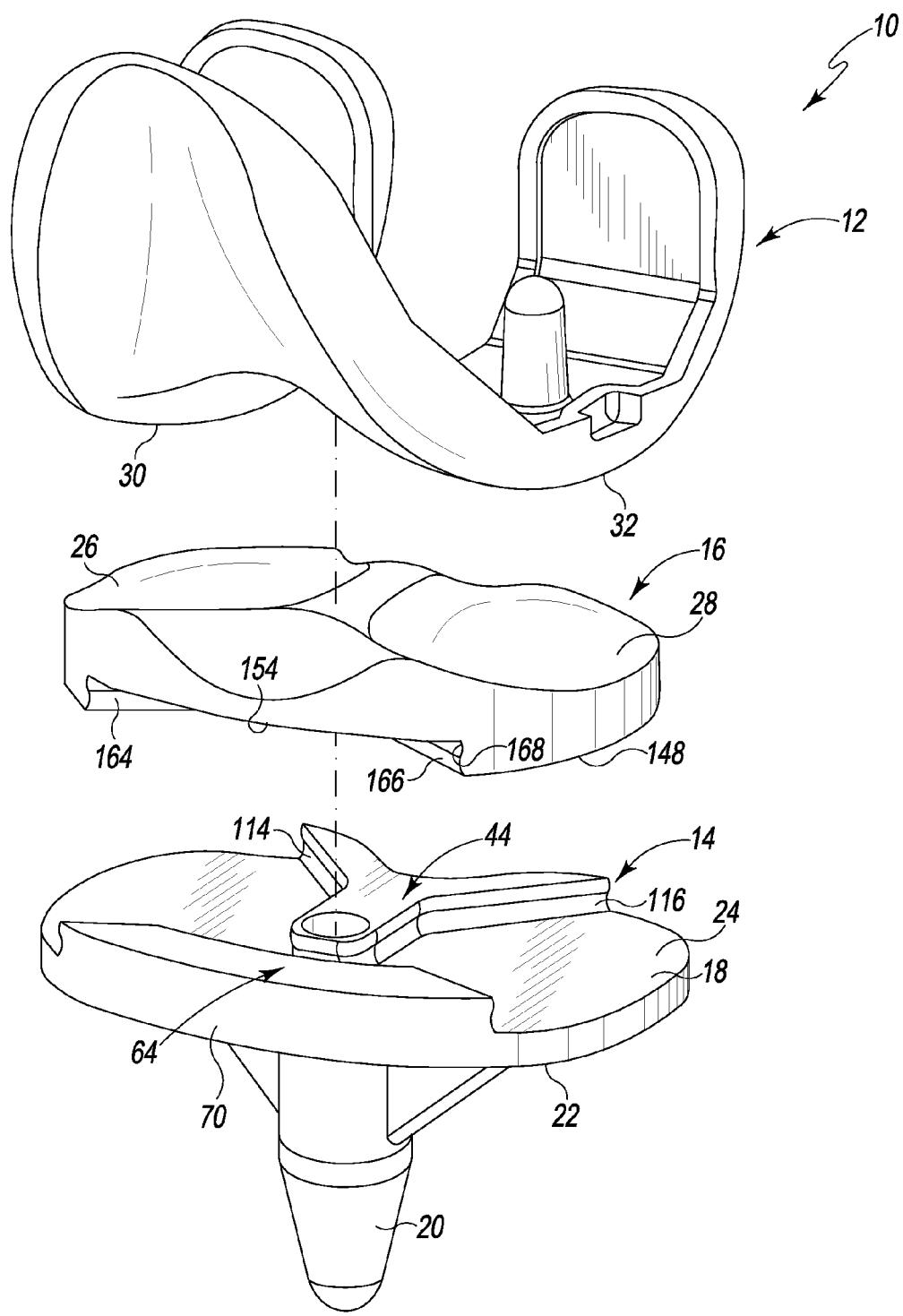
FIG. 1 is an exploded perspective view of a fixed-bearing knee prosthesis.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring now to FIGS. 1-4, there is shown a fixed-bearing knee prosthesis 10. The knee prosthesis 10 includes a femoral component 12, a tibial tray 14, and a tibial bearing 16. The tibial tray 14 includes a platform 18 having a fixation member, such as an elongated stem 20, extending away from its inferior surface 22. The elongated tibial stem 20 is configured to be implanted into a surgically prepared end of a patient's tibia (not shown). It should be appreciated that other fixation members, such as one or more short pegs or posts, may be used in lieu of the elongated stem 20. The bearing 16 is securable to the tibial tray 14. In particular, as will be discussed below in greater detail, the bearing 16 may be snap-fit to the tibial tray 14. In such a way, the bearing 16 is fixed relative to the tibial tray 14 (i.e., it is not rotatable or moveable in the anterior/posterior or medial/lateral directions).

The superior surface of the bearing 16 includes a lateral bearing surface 26 and a medial bearing surface 28. The bearing surfaces 26, 28 are configured to articulate with a lateral condyle surface 30 and a medial condyle surface 32, respectively, of the femoral component 12. Specifically, the femoral component 12 is configured to be implanted into a surgically prepared end of the patient's femur (not shown), and is configured to emulate the configuration of the patient's natural femoral condyles. As such, the lateral condyle surface 30 and the medial condyle surface 32 are configured (e.g., curved) in a manner which mimics the condyles of the natural femur. The lateral condyle surface 30 and the medial condyle surface 32 are spaced apart from one another thereby defining an intercondylar notch therebetween.

The components of the knee prosthesis 10 that engage the natural bone, such as the femoral component 12 and the tibial tray 14, may be constructed with a biocompatible metal, such as a cobalt chrome alloy, although other materials may also be used. The bone engaging surfaces of these components may be textured to facilitate cementing the component to the bone. Such surfaces may also be porous coated to promote bone ingrowth for permanent fixation.

The bearing 16 may be constructed with a material that allows for smooth articulation between the bearing 16 and the femoral component 12, such as a polymeric material. One such polymeric material is polyethylene such as ultra-high molecular weight polyethylene (UHMWPE).

Figure 2:
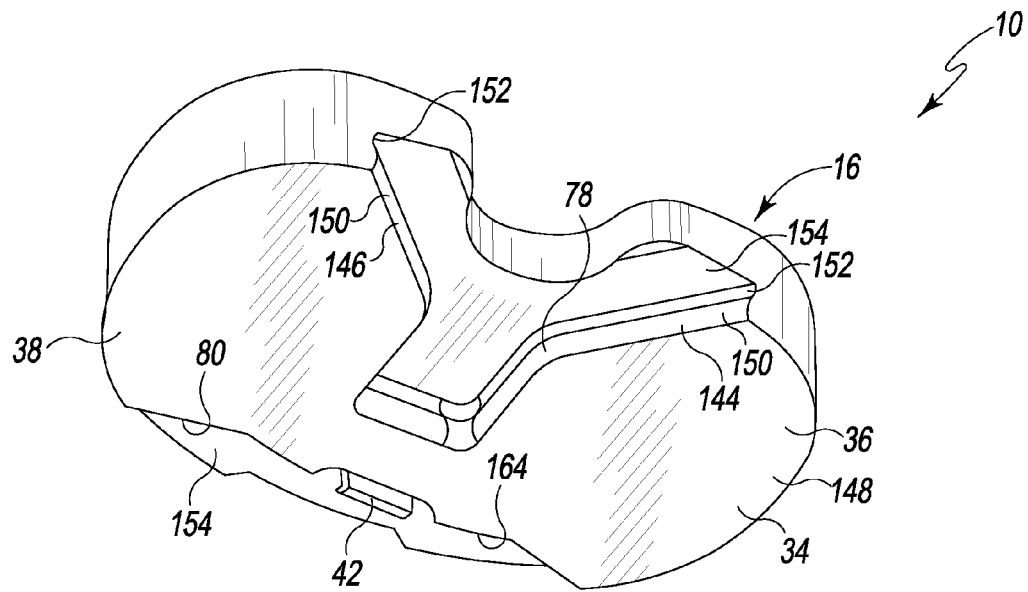
FIG. 2 is a bottom perspective view of the bearing of the knee prosthesis of FIG. 1.

As shown in FIG. 2, the inferior surface 36 of the bearing 16 includes a lateral pedestal 34 and a medial pedestal 38. An anterior tab 42 is also defined in the bearing 16.

Figure 3:
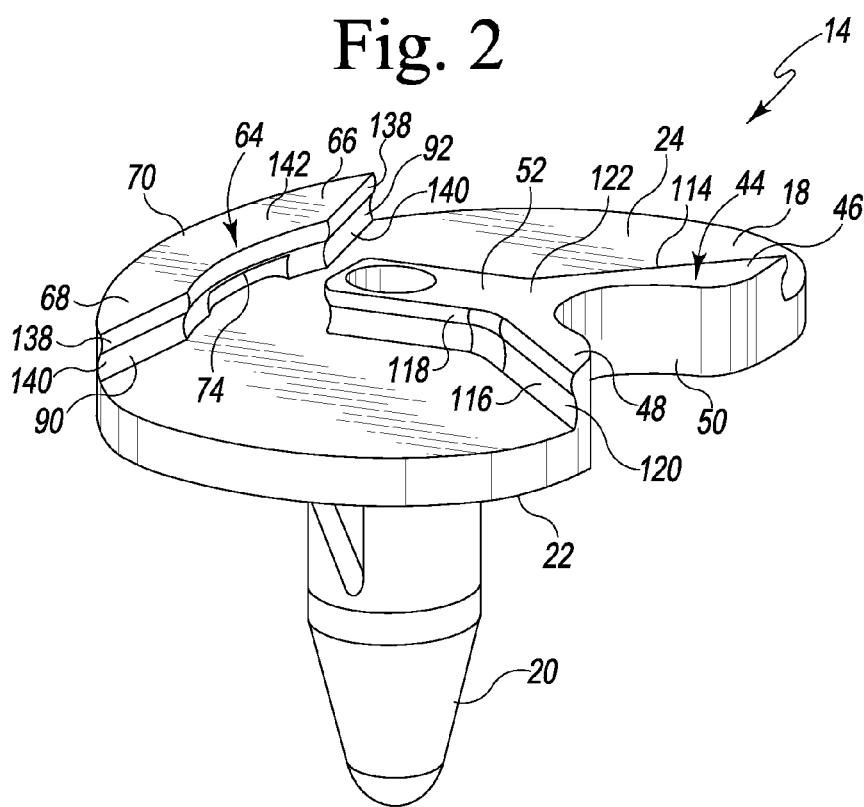
FIG. 3 is a perspective view of the tibial tray of the knee prosthesis of FIG. 1.
Figure 4:
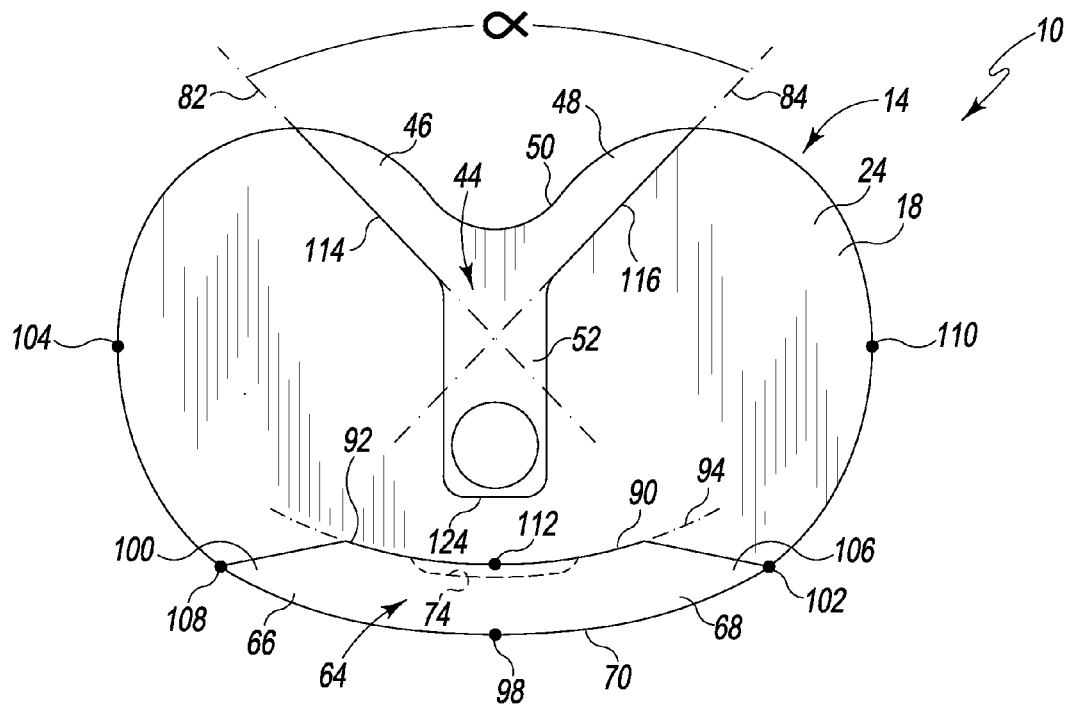
FIG. 4 is a plan view of the tibial tray of the knee prosthesis of FIG. 1.

As shown in FIGS. 3 and 4, a generally Y-shaped posterior buttress 44 extends upwardly from the superior surface 24 of the tibial tray 14. In the illustrative embodiment described herein, the posterior buttress 44 has a pair of arms 46, 48 extending along a posterior section of the perimeter of tibial tray's platform 18. Specifically, the lateral arm 46 of the posterior buttress 44 extends along the posterior edge 50 on the lateral side of the platform 18, whereas the medial arm 48 of the posterior buttress 44 extends along the posterior edge 50 on the medial side of the platform 18 in a direction away from the lateral arm 46. A third arm 52 of the posterior buttress 44 extends anteriorly away from the intersection of the lateral arm 46 and the medial arm 48 (i.e., in a direction toward the center of the platform 18).

As also shown in FIGS. 3 and 4, an anterior buttress 64 extends upwardly from the superior surface 24 of the tibial tray 14. In the illustrative embodiment described herein, the anterior buttress 64 has a pair of arms 66, 68 extending along an anterior section of the perimeter of tibial tray's platform 18. Specifically, the lateral arm 66 of the anterior buttress 64 extends along the anterior edge 70 on the lateral side of the platform 18, whereas the medial arm 68 of the anterior buttress 64 extends along the anterior edge 70 on the medial side of the platform 18 in a direction away from the lateral arm 66.

The anterior buttress 64 defines a continuous, monolithic structure in which proximal ends of the lateral and medial arms 66, 68 are conjoined (i.e., spatially secured to one another) at location on the anterior edge 70 at the anterior-most point 98 of the tray's platform 18. The lateral arm 66 extends laterally away from the anterior-most point 98 of the tray's platform and terminates at its lateral end 100 located at a point 102 on the anterior edge 70 of the platform 18 between the anterior-most point 98 of the tray's platform and the lateral-most point 104 of the tray's platform. The medial arm 68 extends medially away from the anterior-most point 98 of the tray's platform and terminates at its medial end 106 located at a point 108 on the anterior edge 70 of the platform 18 between the anterior-most point 98 of the tray's platform and the medial-most point 110 of the tray's platform.

The posterior-most edge 90, 92 of the anterior buttress 64 is curved (i.e., arcuate-shaped). In particular, as shown most clearly in FIG. 4, the imaginary line 94 extending along the posterior-most edge 90 of the lateral arm 66 and the posterior-most edge 92 of the medial arm 68 is curved along a constant radius. It should be appreciated that since the arms 66, 68 of the anterior buttress 64 are contiguous, the posterior-most edge 90 of the lateral arm 66 and the posterior-most edge 92 of the medial arm 68 define a single, continuous, uninterrupted edge 90, 92.

In the illustrative embodiment described herein, the anterior buttress 64 of the knee prosthesis 10 is discontiguous with the posterior buttress 44. In other words, the buttresses 44, 64 are spaced apart from one another such that there is a gap therebetween. However, other embodiments are contemplated, including arrangements in which the buttresses are contiguous with one another. Moreover, the two buttresses 44, 64 are herein described as being of a similar height, although the buttresses could be embodied has having dissimilar heights.

The anterior buttress 64 includes an anterior undercut 74. The anterior undercut 74 is centered on the intersection of the two arms 66, 68 defining the anterior buttress 64. In other words, the imaginary line 94 extending along the posterior-most edge 90 of the lateral arm 66 and the posterior-most edge 92 of the medial arm 68 has a midpoint 112. The anterior undercut 74 is centered on the midpoint 112. As will be described below, the anterior tab 42 of the bearing 16 is sized and positioned to be received into the anterior undercut 74 of the anterior buttress 64 to facilitate locking the bearing 16 to the tibial tray 14.

Figure 5:
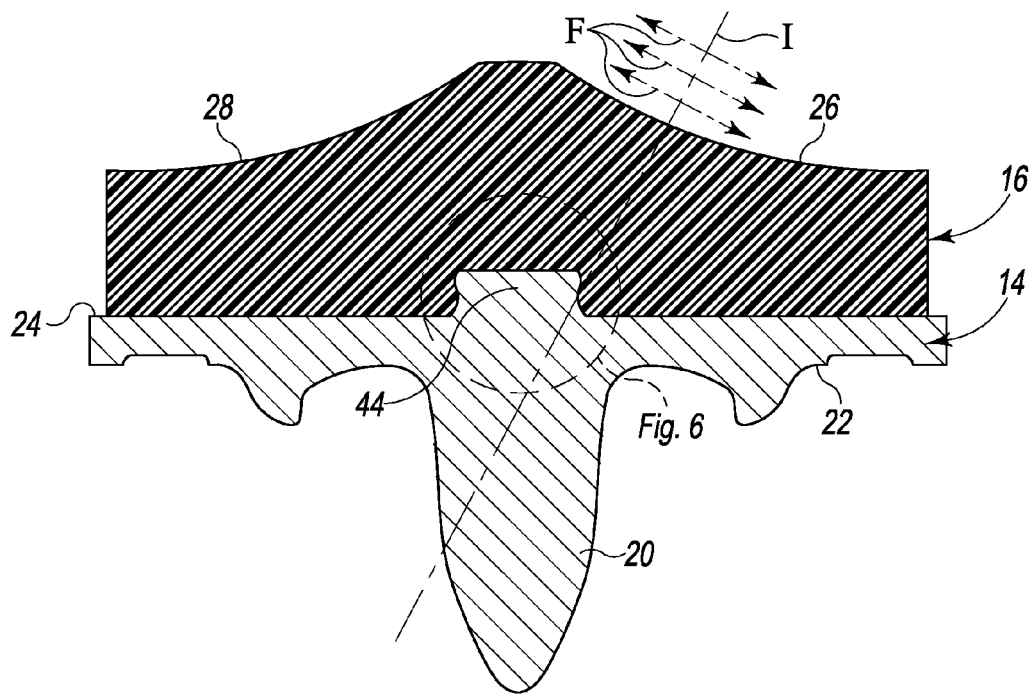
FIG. 5 is a cross sectional view showing the tibial bearing snap fit to the tibial tray.
Figure 6:
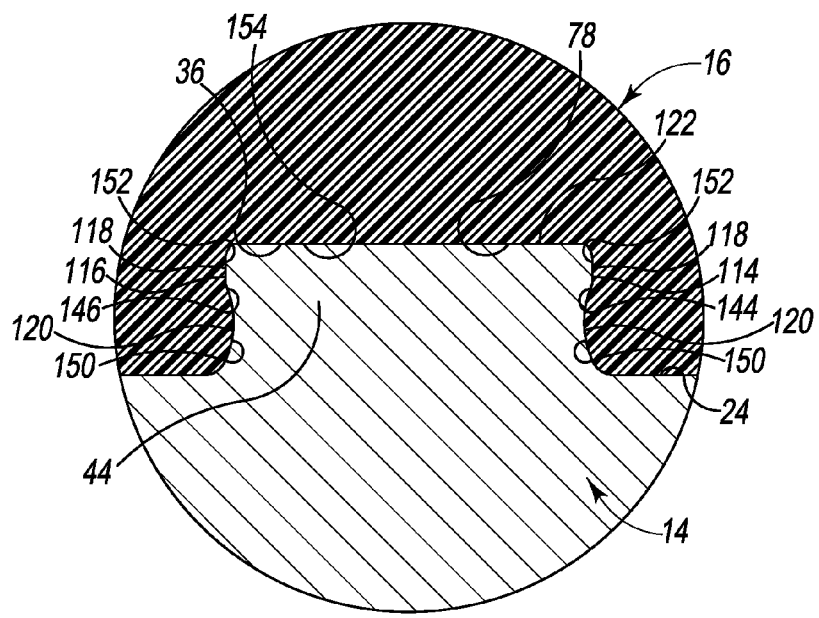
FIG. 6 is an enlarged view showing in greater detail the area encircled in FIG. 5.

As can be seen in FIGS. 3, 5, and 6, the vertical sidewalls of the posterior buttress 44 and the anterior buttress 64 have an S-shaped (or reverse S-shaped depending on the viewed perspective) profile. Specifically, both the lateral-most edge 114 and the medial-most edge 116 of the posterior buttress 44 include a convex surface 118 that transitions to a concave surface 120. In particular, both edges 114, 116 extend from the superior surface 24 of the tibial tray 14 to a superior-most surface 122 of the posterior buttress 44. The convex surface 118 of each of the lateral-most edge 114 and the medial-most edge 116 extends inferiorly from the superior-most surface 122 and transitions to the respective concave surface 120 of each of the lateral-most edge 114 and the medial-most edge 116. In turn, the concave surface 120 of each of the lateral-most edge 114 and the medial-most edge 116 extends inferiorly from their respective convex surfaces 118 and transitions to the superior surface 24 of the tibial tray 14.

As can be seen in FIGS. 3 and 4, the S-shaped (or reverse S-shaped depending on the viewed perspective) edges 114, 116 extend along the anterior/posterior length of the posterior buttress 44. In particular, the lateral-most edge 114 of the posterior buttress 44 extends anteriorly away from the posterior edge 50 of the tibial tray's platform 18 along the lateral arm 46 of the posterior buttress 44 and transitions to the posterior buttress's third arm 52. The lateral-most edge 114 then extends anteriorly away from the lateral arm 46 along the third arm 52 of the posterior buttress 44 and transitions to the posterior buttress's anterior-most edge 124. Similarly, the medial-most edge 116 of the posterior buttress 44 extends anteriorly away from the posterior edge 50 of the tibial tray's platform 18 along the medial arm 48 of the posterior buttress 44 and transitions to the other side of the posterior buttress's third arm 52. The medial-most edge 116 then extends anteriorly away from the medial arm 48 along the third arm 52 of the posterior buttress 44 and transitions to the posterior buttress's anterior-most edge 124 where it conjoins the lateral-most edge 114.

In a similar fashion to the vertical surfaces of the posterior buttress 44, the posterior-most edge 90, 92 of the anterior buttress 64 includes a convex surface 138 that transitions to a concave surface 140. In particular, as shown in FIG. 3, the posterior-most edge 90, 92 of the anterior buttress 64 extends from the superior surface 24 of the tibial tray 14 to a superior-most surface 142 of the anterior buttress 64. The convex surface 138 of the posterior-most edge 90, 92 of the anterior buttress 64 extends inferiorly from the superior-most surface 122 and transitions to the concave surface 140 of the posterior-most edge 90, 92 of the anterior buttress 64. In turn, the concave surface 140 of the posterior-most edge 90, 92 of the anterior buttress 64 extends inferiorly from the convex surface 138 and transitions to the superior surface 24 of the tibial tray 14.

As can be seen in FIGS. 3 and 4, the S-shaped (or reverse S-shaped depending on the viewed perspective) posterior-most edge 90, 92 of the anterior buttress 64 extends along the medial/lateral length of the anterior buttress 64. In particular, the posterior-most edge 90, 92 of the anterior buttress 64 extends from the lateral end 100 of the lateral arm 66 to the medial end 106 of the medial arm 68.

As shown in FIG. 2, the inferior surface 36 of the bearing 16 has a posterior recess 78 and an anterior recess 80 defined therein. The posterior recess 78 is configured to compliment the shape of the posterior buttress 44 of the tibial tray 14. That is, when the bearing 16 is secured to the tibial tray 14, the sidewalls of the pedestals 34, 38 which define the posterior recess 78 snap to the edges of the posterior buttress 44. In particular, the posterior recess 78 is defined in part by a lateral-most sidewall 144 and a medial-most sidewall 146. A superior-most surface 154 of the inferior surface 36 of the bearing 16 defines the superior boundary of the posterior recess 78. The lateral-most sidewall 144 and a medial-most sidewall 146 of the bearing's posterior recess 78 have an S-shaped (or reverse S-shaped depending on the viewed perspective) profile which compliments the similarly-shaped profiles of the lateral-most edge 114 and the medial-most edge 116 of the tibial tray's posterior buttress 44. Specifically, both the lateral-most sidewall 144 and the medial-most sidewall 146 of the posterior recess 78 extend superiorly from an inferior-most surface 148 of the bearing 16. As can be seen in FIG. 2, both sidewalls 144, 146 include a convex surface 150 that extends superiorly from the inferior-most surface 148 of the bearing 16 and transitions to a concave surface 152. The concave surface 152 of the sidewalls 144 transitions to the superior-most surface 154 of the inferior surface 36 of the bearing 16.

Similarly, the anterior recess 80 is configured to compliment the shape of the anterior buttress 64 of the tibial tray 14. That is, when the bearing 16 is secured to the tibial tray 14, the sidewalls of the pedestals 34, 38 which define the anterior recess 80 snap to the edges of the anterior buttress 64. In particular, the anterior recess 80 is defined in part by a posterior-most sidewall 164. Similarly to the posterior recess 78, the superior-most surface 154 of the inferior surface 36 of the bearing 16 defines the superior boundary of the anterior recess 80. As shown in FIG. 1, the posterior-most sidewall 164 of the bearing's anterior recess 80 has an S-shaped (or reverse S-shaped depending on the viewed perspective) profile which compliments the similarly-shaped profile of the posterior-most edge 90, 92 of the tibial tray's anterior buttress 64. Specifically, the posterior-most sidewall 164 of the bearing's anterior recess 80 extends superiorly from the inferior-most surface 148 of the bearing 16. As can be seen in FIG. 1, the posterior-most sidewall 164 of the bearing's anterior recess 80 includes a convex surface 166 that extends superiorly from the inferior-most surface 148 of the bearing 16 and transitions to a concave surface 168. The concave surface 168 of the posterior-most sidewall 164 transitions to the superior-most surface 154 of the inferior surface 36 of the bearing 16.

The dimensions of the bearing's recesses 78, 80 and the tibial tray's buttresses 44, 64 are selected such that a relatively tight fit is achieved. In such a way, the bearing 16 is fixed relative to the tibial tray 14. In particular, the configuration of the buttresses 44, 64 and the pedestals 34, 38 formed in the inferior surface 36 of the bearing 16 prevent movement of the bearing 16 relative the tibial tray 14 in the anterior/posterior direction and the medial/lateral direction. Moreover, the S-shaped profiles utilized in the construction of the tray/bearing interface (i.e., the S-shaped profiles of the tray's buttresses 44, 64 and the bearing's recesses 78, 80) prevent lift off of the bearing 16 from the tibial tray 14. In particular, such concave/convex S-shaped profiles provide interference at specific locations along the tray/bearing interface to generate force in opposing directions (such interference being shown by the imaginary line (I) in FIG. 5). These opposing forces (shown by the imaginary vectors (F) in FIG. 5) are out of plane with (i) the sides of the buttresses 44, 46 and the pedestals 34, 38 and (ii) the horizontal planes of the superior surface 24 of the tibial tray 14 and the inferior-most surface 148 of the bearing 16. Such out-of-plane arrangement of the opposing forces drives the bearing 16 downwardly (i.e., inferiorly) serving to minimize lift-off and providing the necessary hold down between the insert/tray interface. Moreover, rotational micromotion is reduced, if not prevented all together, by the relatively tight snap-fit arrangement of the buttresses 44, 64 of the tibial tray 14 into the recesses 78, 80 of the bearing 16.

To secure the tibial bearing 16 to the tibial tray 14, the posterior portion of the bearing 16 is positioned in contact with the posterior portion of the tibial tray 14. Thereafter, the anterior portion of the tibial bearing 16 is advanced downwardly toward the tibial tray 14 such that the anterior tab 42 of the tibial bearing 16 is deflected by the anterior buttress 64 and thereafter snapped into the anterior undercut 74 of the anterior buttress thereby securing the bearing 16 to the tray 14. In doing so, the lateral-most sidewall 144 and the medial-most sidewall 146 of the bearing's posterior recess 78 are snap locked to the lateral-most edge 114 and the medial-most edge 116 of the tibial tray's posterior buttress 44, respectively. Similarly, the posterior-most sidewall 164 of the bearing's anterior recess 80 is snap locked to the posterior-most edge 90 of the tibial tray's anterior buttress 64.

As alluded to above, in the illustrative embodiment described herein, the posterior buttress 44 is embodied as a generally Y-shaped structure having a pair of arms 46, 48 extending in opposite directions along the posterior edge 50 of the tray's platform 18, with a third arm 52 extending anteriorly from the posterior edge 50 of the tibial tray 14 (i.e., in a direction toward the center of the tray's platform 18). As shown in FIG. 4, an imaginary line 82 extends along the lateral-most edge 114 of the lateral arm 46 and intersects an imaginary line 84 that extends along the medial-most edge 116 of the medial arm 48 to define an angle of intersection ($\alpha$). In the exemplary embodiments described herein, the angle of intersection ($\alpha$) is between 45-145°. In more specific illustrative embodiments, the angle of intersection ($\alpha$) is between 60-120°. In one such specific illustrative embodiment, the angle of intersection ($\alpha$) is approximately 90°. It should be appreciated that increasing the angle of intersection ($\alpha$) reduces micromotion, while decreasing the angle of intersection ($\alpha$) increases the load bearing surface area of the tibial tray 14. Although other configurations may be utilized, it has been found that arranging the arms 46, 48 of the posterior buttress 44 as described above (i.e., having an angle of intersection ($\alpha$) between 60-120°) provides an unexpectedly beneficial working balance between these two considerations. On particularly well-balanced arrangement of the posterior buttress 44 is found in the illustrative embodiment where the angle of intersection ($\alpha$) is approximately 90°.

Figure 7:
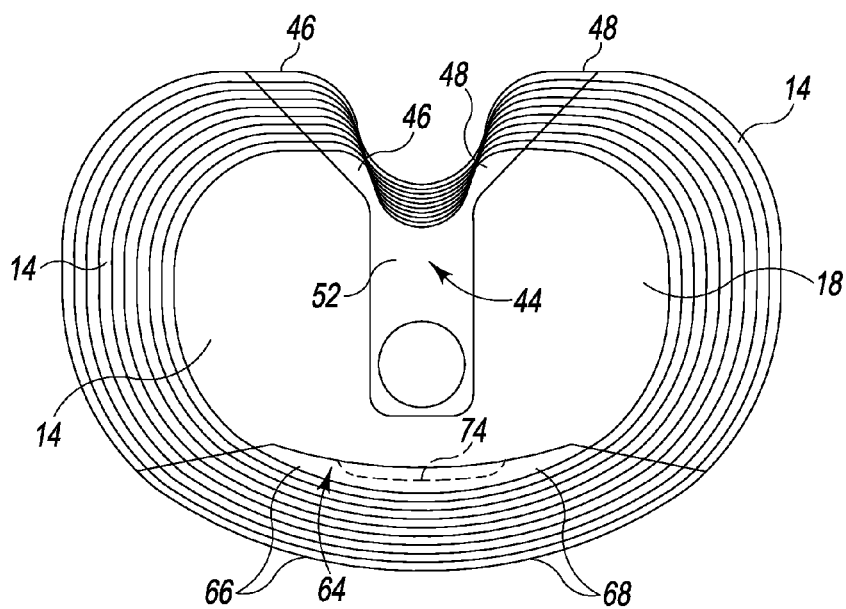
FIG. 7 is a diagrammatic plan view of a number of differently sized tibial trays of the knee prosthesis of FIG. 1.

A given design of a fixed-bearing knee prosthesis is typically made commercially available in a variety of different sizes, particularly in a variety of different widths. This is done to accommodate the many variations in patient size and anatomy across a population. However, the configuration of the fixed-knee prosthesis 10 of the present disclosure allows for a high degree of flexibility in regard to the sizing of the tibial tray 14 and the bearing 16. In particular, FIG. 7 is a diagrammatic representation of a plurality of differently-sized tibial trays 14 superimposed upon one another. As can be seen, despite each of the individual trays 14 having a size (e.g., width) that is different from the other trays 14 of the group, the basic configuration of the posterior buttress 44 and the anterior buttress 64 remains the same across the range of differently-sized trays 14. For example, the location of the undercut 74 defined in the anterior buttress 64 remains the same across the range of differently-sized trays 14, although the width of the anterior buttress's arms 66, 68 is varied to accommodate the overall width of a given tray 14. As shown in FIG. 7, the size and configuration of the third arm 52 of the posterior buttress 44 remains unchanged across the range of differently-sized trays 14.

Differently-sized bearings 16 may also be configured in such a manner. In particular, a plurality of the bearings 16 may be designed with each of such a plurality of bearings 16 having a different size, particularly a different width. However, each of such differently-sized bearings 16 may include mating features that are commonly-sized and commonly-located with the commonly-sized and commonly-located features of the tibial tray 14 described above. In particular, each of the bearings 16 across a range of differently-sized bearings 16 may include a posterior recess 78 and an anterior recess 80 that is positioned and sized to tightly fit against the edges of the posterior buttress 44 and the anterior buttress 64, respectively, of each of the tibial trays 14 across the range of differently-sized trays 14. In doing so, the anterior tab 42 is commonly-sized and commonly-located across the range of differently-sized bearings 16 so that it is positioned in the anterior undercut 74 of each of the tibial trays 14 across the range of differently-sized trays 14.

It should be appreciated from the above-discussion that the general configuration of the buttresses 44, 64 is the same across the range of differently-sized tibial trays 14. Likewise, the general configuration of the recesses 78, 80 and the general configuration of tabs 42 are the same across the range of differently-sized bearings 16. As such, any size bearing 16 may be secured to any size tibial tray 14. This provides the orthopaedic surgeon with greater flexibility of matching the knee prosthesis 10 to a particular patient's anatomy.

It should also be appreciated that other configurations of locking tabs may be used in the design of the knee prosthesis 10. In particular, the tibial bearing 16 may be embodied with additional locking tabs similar to the anterior locking tab 42. Such locking tabs may be arranged on the tibial bearing 16 to be received into undercuts formed in the lateral-most edge 114 and the medial-most edge 116 of the tibial tray's posterior buttress 44. Such tabs could be used in addition to, or in lieu of, the anterior tab 42. Alternatively, the knee prosthesis 10 may be designed without the use of any locking tabs. In such a case, the snap-fit arrangement of the buttresses 44, 64 of the tibial tray 14 into the recesses 78, 80 of the bearing 16 provide the sole source of mechanical interlocking between the tibial tray 14 and the bearing 16.

As described herein, the various designs of the knee prosthesis 10 allow for the enhanced interchangeability of differently-sized components. In particular, any one of a plurality of differently-sized bearings may be secured to any one of a plurality of differently-sized tibial trays. As a result, articulation surface geometries and other features of the bearing may be enhanced for each size of femoral component. Such interchangeability also allows for smaller size increments in the design of a range of femoral components.

It should also be appreciated that although the concave/convex S-shaped profiles have herein been described in the context of the tray/bearing interface of the fixed-bearing knee prosthesis 10, such an arrangement may be used in the construction of other types of orthopaedic prostheses such as a hip, shoulder, or ankle prosthesis.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure as defined by the appended claims.

The invention claimed is:

1. A fixed-bearing knee prosthesis, comprising:
   a femoral component having a medial condyle surface and a lateral condyle surface,
   a bearing having (i) a medial bearing surface configured to articulate with the medial condyle surface of the femoral component, and (ii) a lateral bearing surface configured to articulate with the lateral condyle surface of the femoral component, and
   a tibial tray secured to the bearing, the tibial tray having a platform with a fixation member extending inferiorly from an inferior surface thereof, the platform having a posterior buttress extending anteriorly away from a posterior section of a perimeter of the platform and extending superiorly from a superior surface of the platform, wherein the posterior buttress is generally Y-shaped and comprises:
   a first arm extending along a posterior edge of the platform,
   a second arm extending along the posterior edge of the platform in a direction away from the first arm,
   a third arm extending anteriorly away from the first arm and the second arm,
   a lateral-most edge that is defined in the first arm and the third arm such that the lateral-most edge of the posterior buttress extends anteriorly away from the posterior edge of the platform along the first arm and the third arm, the lateral-most edge having a convex surface that faces outward from the first arm and the third arm and transitions to a concave surface that faces outward from the first arm and the third arm, the convex surface of the lateral-most edge being positioned superior to the concave surface of the lateral-most edge, and
   a medial-most edge that is defined in the second arm and the third arm such that the medial-most edge of the posterior buttress extends anteriorly away from the posterior edge of the platform along the second arm and the third arm, the medial-most edge having a convex surface that faces outward from the second arm and the third arm and transitions to a concave surface that faces outward from the second arm and the third arm, the convex surface of the medial-most edge being positioned superior to the concave surface of the medial-most edge.

2. The knee prosthesis of claim 1, wherein:
the posterior buttress of the tibial tray comprises a superior-most surface,
the posterior buttress extends superiorly from the superior surface of the platform to the superior-most surface of the posterior buttress,
the convex surface of the lateral-most edge of the posterior buttress extends inferiorly from the superior-most surface of the posterior buttress and transitions to the concave surface of the lateral-most edge of the posterior buttress, and
the convex surface of the medial-most edge of the posterior buttress extends inferiorly from the superior-most surface of the posterior buttress and transitions to the concave surface of the medial-most edge of the posterior buttress.

3. The knee prosthesis of claim 2, wherein:
the concave surface of the lateral-most edge of the posterior buttress extends inferiorly from the convex surface of the lateral-most edge of the posterior buttress and transitions to the superior surface of the platform, and
the concave surface of the medial-most edge of the posterior buttress extends inferiorly from the convex surface of the medial-most edge of the posterior buttress and transitions to the superior surface of the platform.

4. The knee prosthesis of claim 1, wherein:
the posterior buttress of the tibial tray comprises an anterior-most edge,
the lateral-most edge of the posterior buttress extends anteriorly away from the first arm along the third arm of the posterior buttress and transitions to the anterior-most edge of the posterior buttress, and
the medial-most edge of the posterior buttress extends anteriorly away from the second arm along the third arm of the posterior buttress and transitions to the anterior-most edge of the posterior buttress, the anterior-most edge having a convex surface that transitions to a concave surface, the convex surface of the anterior-most edge being positioned superior to the concave surface of the anterior-most edge.

5. The knee prosthesis of claim 1, wherein:
the bearing has a superior surface and an inferior surface,
both the medial bearing surface and the lateral bearing surface are defined in the superior surface of the bearing,
the inferior surface of the bearing contacts the superior surface of the platform of the tibial tray,
the inferior surface of the bearing has a posterior recess formed therein, and
the posterior buttress of the tibial tray is positioned in the posterior recess of the bearing.

6. The knee prosthesis of claim 5, wherein:
the posterior recess of the bearing is defined by (i) a lateral-most sidewall that extends superiorly from an inferior-most surface of the bearing, and (ii) a medial-most sidewall that extends superiorly from the inferior-most surface of the bearing,
the lateral-most sidewall comprises a convex surface that transitions to a concave surface, and
the medial-most sidewall comprises a convex surface that transitions to a concave surface.

7. The knee prosthesis of claim 6, wherein:
the convex surface of the lateral-most sidewall of the posterior recess extends superiorly from the inferior-most surface of the bearing and transitions to the concave surface of the lateral-most sidewall of the posterior recess, and
the convex surface of the medial-most sidewall of the posterior recess extends superiorly from the inferior-most surface of the bearing and transitions to the concave surface of the medial-most sidewall of the posterior recess.

8. A fixed-bearing knee prosthesis, comprising:
a femoral component having a medial condyle surface and a lateral condyle surface,
a bearing having (i) a medial bearing surface configured to articulate with the medial condyle surface of the femoral component, (ii) a lateral bearing surface configured to articulate with the lateral condyle surface of the femoral component, (iii) a locking tab, and
a tibial tray secured to the bearing, the tibial tray having a platform with a fixation member extending inferiorly from an inferior surface thereof, the platform having an anterior buttress extending along an anterior section of a perimeter of the platform and extending superiorly from a superior surface of the platform, wherein the anterior buttress comprises a posterior-most edge having (i) a convex surface that transitions to a concave surface, the convex surface being positioned superior to the concave surface, and (ii) an undercut defined in the concave surface,
wherein (i) an imaginary line extends along the posterior-most edge of the anterior buttress, and the imaginary line defines a curve having a constant radius, (ii) the undercut defined in the anterior buttress is centered on the midpoint of the imaginary line, and (iii) the locking tab of the bearing is positioned in the undercut defined in the anterior buttress.

9. The knee prosthesis of claim 8, wherein:
the anterior buttress of the tibial tray comprises a superior-most surface,
the anterior buttress extends superiorly from the superior surface of the platform to the superior-most surface of the anterior buttress, and
the convex surface of the posterior-most edge of the anterior buttress extends inferiorly from the superior-most surface of the anterior buttress and transitions to the concave surface of the posterior-most edge of the anterior buttress.

10. The knee prosthesis of claim 9, wherein the concave surface of the posterior-most edge of the anterior buttress extends inferiorly from the convex surface of the posterior-most edge of the anterior buttress and transitions to the superior surface of the platform.

11. The knee prosthesis of claim 8, wherein:
the bearing has a superior surface and an inferior surface,
both the medial bearing surface and the lateral bearing surface are defined in the superior surface of the bearing,
the inferior surface of the bearing contacts the superior surface of the platform of the tibial tray,
the inferior surface of the bearing has an anterior recess formed therein, and
the anterior buttress of the tibial tray is positioned in the anterior recess of the bearing.

12. The knee prosthesis of claim 11, wherein:
the anterior recess of the bearing is defined by a posterior-most sidewall that extends superiorly from an inferior-most surface of the bearing, and
the posterior-most sidewall comprises a convex surface that transitions to a concave surface.

13. The knee prosthesis of claim 12, wherein the convex surface of the posterior-most sidewall of the anterior recess extends superiorly from the inferior-most surface of the bearing and transitions to the concave surface of the posterior-most sidewall of the anterior recess.

14. The knee prosthesis of claim 8, wherein:
a medial end of the anterior buttress is located at a location on an anterior edge of the platform between an anterior-most point of the platform and a medial-most point of the platform, and
a lateral end of the anterior buttress is located at a location on an anterior edge of the platform between the anterior-most point of the platform and a lateral-most point of the platform.

15. The knee prosthesis of claim 8, wherein the tibial tray includes a posterior buttress that extends anteriorly away from a posterior section of a perimeter of the platform and extends superiorly from a superior surface of the platform, the posterior buttress being generally Y-shaped and comprising:

a first arm extending along a posterior edge of the platform,
a second arm extending along the posterior edge of the platform in a direction away from the first arm,
a third arm extending anteriorly away from the first arm and the second arm,
a lateral-most surface that is formed on the first arm and the third arm such that the lateral-most surface of the posterior buttress extends anteriorly away from the posterior edge of the platform along the first arm and the third arm, the lateral-most surface including a convex surface formed on the first arm and the third arm that transitions to a concave surface, the convex surface of the lateral-most edge being positioned superior to the concave surface of the lateral-most edge, and
a medial-most surface that is formed on the second arm and the third arm such that the medial-most surface of the posterior buttress extends anteriorly away from the posterior edge of the platform along the second arm and the third arm, the medial-most surface including a convex surface formed on the first arm and the third arm that transitions to a concave surface, the convex surface of the medial-most edge being positioned superior to the concave surface of the medial-most edge.

* * * * *